United States Patent
Andrews et al.

(10) Patent No.: US 6,800,652 B2
(45) Date of Patent: Oct. 5, 2004

(54) DIARYL COMPOUNDS

(75) Inventors: Mark David Andrews, Sandwich (GB); David Hepworth, Sandwich (GB); Donald Stuart Middleton, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/632,355

(22) Filed: Jul. 31, 2003

(65) Prior Publication Data

US 2004/0097509 A1 May 20, 2004

Related U.S. Application Data

(60) Provisional application No. 60/410,610, filed on Sep. 13, 2002.

(30) Foreign Application Priority Data

Aug. 16, 2002 (GB) .............................. 0219154

(51) Int. Cl.[7] ...................... C07D 213/02; A61K 31/47
(52) U.S. Cl. ...................... 514/357; 514/307; 514/311; 514/351; 514/256; 546/139; 546/152; 546/300; 546/329; 544/242
(58) Field of Search ................................ 514/256, 307, 514/311, 351, 357; 546/139, 152, 300, 329; 544/242

(56) References Cited

FOREIGN PATENT DOCUMENTS

| | | |
|---|---|---|
| DE | 10029371 | 1/2002 |
| EP | 0075752 | 6/1983 |
| WO | WO8101407 | 5/1981 |
| WO | WO9717325 | 5/1997 |
| WO | WO 0059893 A1 * | 10/2000 ......... C07D/239/48 |
| WO | WO0172687 | 4/2001 |

* cited by examiner

*Primary Examiner*—Zinna Northington Davis
(74) *Attorney, Agent, or Firm*—Peter C. Richardson; Gregg C. Benson; Martha G. Munchhof

(57) ABSTRACT

The invention relates to compounds of formula I

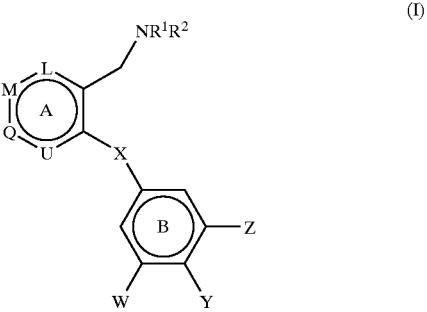

11 Claims, No Drawings

DIARYL COMPOUNDS

This application claims priority from United Kingdom Application No. 0219154.2 filed on Aug. 16, 2002 and U.S. provisional application Ser. No. 60/410,610 filed Sep. 13, 2002.

This invention relates to novel compounds which inhibit monoamine re-uptake. In particular compounds of the present invention exhibit activity as selective serotonin re-uptake inhibitors (SSRIs) and have utility therefore in a variety of therapeutic areas. Notably the compounds of the present invention are useful in the treatment or prevention of a variety of disorders, including those in which the regulation of monoamine transporter function is implicated, such as depression, attention deficit hyperactivity disorder, obsessive-compulsive disorder, post-traumatic stress disorder, substance abuse disorders and sexual dysfunction including premature ejaculation, and to pharmaceutical formulations containing such compounds.

U.S. Pat. Nos. 5,190,965 and 5,430,063 disclose a class of phenoxyphenyl compounds, which are a class of dopamine antagonists. WO 93/12080, WO 97/17325 and EP 0,402, 097 disclose substituted diphenylsulfides, which are serotonin uptake inhibitors. WO 01/72687, WO 00/50380 and WO 01/27068 describe diphenyl ether derivatives, which are selective serotonin re-uptake inhibitors. J. Med. Chem 2002, 45(6), 1253–1258, discloses diphenyl sulfides as selective serotonin transporter ligands.

According to a first aspect the invention provides a compound of general formula (I) or pharmaceutically acceptable salts, solvates or polymorphs thereof;

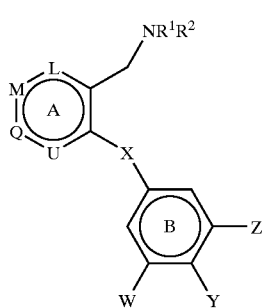

(I)

wherein;

X is S or $CH_2$;

L and U, which may be the same or different, are —N—, —N$^+$(—O$^-$)— or —C(H)—;

M and Q, which may be the same or different, are —N—, —N$^+$(—O$^-$)— or —C(R$^4$)—;

wherein ring A contains 1 or 2 nitrogen atoms, and wherein when L, U, M or Q is —N$^+$(—O$^-$)—, ring A contains no other nitrogen atom;

R$^1$ and R$^2$, which may be the same or different, are hydrogen, $C_1$-$C_8$alkyl, $(CH_2)_m(C_3$-$C_6$cycloalkyl) wherein m=0, 1, 2 or 3, or R$^1$ and R$^2$ together with the nitrogen to which they are attached form an azetidine ring;

W, Y and Z, which may be the same or different, are hydrogen, halogen, $C_1$-$C_6$alkyl, $CF_3$, $OCF_3$, $C_1$-$C_4$alkylthio or $C_1$-$C_4$alkoxy; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; and wherein W, Y and Z are not all hydrogen;

and each R$^4$ is independently:

—(CH$_2$)$_p$—R$^5$;

where p is 0, 1 or 2;

R$^5$ is hydrogen, CONR$^6$R$^7$, SO$_2$NR$^6$R$^7$, SO$_2$NHC(=O)R$^6$, hydroxy, $C_1$-$C_4$alkoxy, NR$^8$SO$_2$R$^9$, NO$_2$, NR$^6$R$^{11}$, CN, CO$_2$R$^{10}$, SR$^{10}$, S(O)R$^9$ or SO$_2$R$^{10}$; R$^6$, R$^7$, R$^8$ and R$^{10}$ which may be the same or different, are hydrogen or $C_1$-$C_6$alkyl optionally substituted independently by one or more R$^{12}$; R$^9$ is $C_1$-$C_6$ alkyl optionally substituted independently by one or more R$^{12}$; R$^{11}$ is hydrogen, $C_1$-$C_6$ alkyl optionally substituted independently by one or more R$^{12}$, C(O)R$^6$, CO$_2$R$^9$, C(O) NHR$^6$ or SO$_2$NR$^6$R$^7$; R$^{12}$ is fluoro, hydroxy, CO$_2$H, $C_3$-$C_6$cycloalkyl, NH$_2$, CONH$_2$, $C_1$-$C_6$alkoxy, $C_1$-$C_6$alkoxycarbonyl or a 5- or 6-membered heterocyclic ring containing 1, 2 or 3 heteroatoms selected from N, S and O optionally substituted independently by one or more R$^{13}$; or R$^6$ and R$^7$, together with the nitrogen to which they are attached, form a 4-, 5- or 6-membered heterocyclic ring optionally substituted independently by one or more R$^{13}$; or a 5- or 6-membered heterocyclic ring containing 1, 2 or 3 heteroatoms selected from N, S and O, optionally substituted independently by one or more R$^{13}$; wherein R$^{13}$ is hydroxy, $C_1$-$C_4$alkoxy, fluoro, $C_1$-$C_6$alkyl, haloalkyl, haloalkoxy, —NH$_2$, —NH($C_1$-$C_6$alkyl) or —N($C_1$-$C_6$alkyl)$_2$; or when both M and Q are CR$^4$, the R$^4$ groups are linked so that together with the interconnecting atoms, the R$^4$ groups form a fused 5- to 7-membered carbocyclic or heterocyclic ring which may be saturated, unsaturated or aromatic.

Unless otherwise indicated, any alkyl group may be straight or branched and is of 1 to 6 carbon atoms, preferably 1 to 4 and particularly 1 to 3 carbon atoms.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, dioxanyl, morpholino, dithianyl, thiomorpholino, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Unless otherwise indicated, any carbocyclyl group contains 3 to 8 ring-atoms, and may be saturated, unsaturated or aromatic. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Preferably, L and U are —CH—.

Preferably, W, Y and Z are each independently selected from hydrogen, methyl, ethyl, $CF_3$, $OCF_3$, $C_1$–$C_4$alkylthio, methoxy, ethoxy, chloro, fluoro and bromo.

Preferably, W and Z are hydrogen.

Preferably, Y is methylthio.

Preferably, M and Q are each independently selected from —N— and —CH—.

More preferably, one of M and Q is —N— and the other is —CH—.

More preferably, L and U are —CH—, one of M and Q is —N— and the other is —CH—.

Preferably, $R^1$ and $R^2$ are each independently selected from hydrogen and $C_1$–$C_6$alkyl.

More preferably, $R^1$ is methyl and $R^2$ is hydrogen or methyl.

Preferred compounds are:

N-methyl-N-[(4-{[4-(methylsulfanyl)phenyl]sulfanyl}-3-pyridinyl)methyl]amine,
N,N-dimethyl-N-[(4-{[4-(methylsulfanyl)phenyl]sulfanyl}-3-pyridinyl)methyl]amine,
N-methyl-N-[(3-{[4-(methylsulfanyl)phenyl]sulfanyl}-4-pyridinyl)methyl]amine,
N,N-dimethyl-N-[(3-{[4-(methylsulfanyl)phenyl]sulfanyl}-4-pyridinyl)methyl]amine,
N-methyl-N-({3-[4-(methylsulfanyl)benzyl]-4-pyridinyl}methyl)amine,
N,N-dimethyl-({3-[4-(methylsulfanyl)benzyl]-4-pyridinyl}methyl)amine,
N-methyl-N-({4-[4-(methylsulfanyl)benzyl]-3-pyridinyl}methyl)amine, and
N,N-dimethyl-N-({4-[4-(methylsulfanyl)benzyl]-3-pyridinyl}methyl)amine.

For the avoidance of doubt, unless otherwise indicated, the term substituted means substituted by one or more defined groups. In the case where groups may be selected from a number of alternatives groups, the selected groups may be the same or different.

For the avoidance of doubt, the term independently means that where more than one substituent is selected from a number of possible substituents, those substituents may be the same or different.

The pharmaceutically or veterinarily acceptable salts of the compounds of formula I which contain a basic centre are, for example, non-toxic acid addition salts formed with inorganic acids such as hydrochloric, hydrobromic, hydroiodic, sulfuric and phosphoric acid, with carboxylic acids or with organo-sulfonic acids. Examples include the HCl, HBr, HI, sulfate or bisulfate, nitrate, phosphate or hydrogen phosphate, acetate, benzoate, succinate, saccharate, fumarate, maleate, lactate, citrate, tartrate, gluconate, camsylate, methanesulfonate, ethanesulfonate, benzenesulfonate, p-toluenesulfonate and palmoate salts. Compounds of formula I can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For reviews on suitable pharmaceutical salts see Berge et al, J. Pharm. Sci., 66, 1–19, 1977; Bighley et al, International Journal of Pharmaceutics, 33 (1986), 201–217; and P L Gould, Encyclopedia of Pharmaceutical Technology, Marcel Debker Inc, New York 1996, Volume 13, page 453–497.

The pharmaceutically acceptable solvates of the compounds of the invention include the hydrates thereof.

Also included within the scope of the compound and various salts of the invention are polymorphs thereof.

Hereinafter, compounds their pharmaceutically acceptable salts, their solvates or polymorphs, defined in any aspect of the invention (except intermediate compounds in chemical processes) are referred to as "compounds of the invention".

The compounds of the invention have the advantage that they are selective inhibitors of the re-uptake of serotonin (SRIs) (and so are likely to have reduced side effects), they have a rapid onset of action (making them suitable for administration shortly before an effect is required), they have desirable potency and associated properties. Compounds that selectively inhibit the re-uptake of serotonin, but not noradrenaline or dopamine, are preferred.

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of the invention.

The compounds of the invention may exist in one or more tautomeric forms. All tautomers and mixtures thereof are included in the scope of the present invention. For example, a claim to 2-hydroxypyridinyl would also cover its tautomeric form, α-pyridonyl.

The invention also includes radiolabelled compounds.

It will be appreciated by those skilled in the art that certain protected derivatives of compounds of the invention, which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". Further, certain compounds of the invention may act as prodrugs of other compounds of the invention.

All protected derivatives and prodrugs of compounds of the invention are included within the scope of the invention. Examples of suitable pro-drugs for the compounds of the present invention are described in Drugs of Today, Volume 19, Number 9, 1983, pp 499–538 and in Topics in Chemistry, Chapter 31, pp 306–316 and in "Design of Prodrugs" by H. Bundgaard, Elsevier, 1985, Chapter 1 (the disclosures in which documents are incorporated herein by reference).

It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Preferred prodrugs for compounds of the invention include: esters, carbonate esters, hemi-esters, phosphate esters, nitro esters, sulfate esters, sulfoxides, amides, carbamates, azo-compounds, phosphamides, glycosides, ethers, acetals and ketals.

Compounds of the invention may be prepared, in known manner in a variety of ways. In the following reaction schemes and hereafter, unless otherwise stated $R^1$ to $R^{13}$, L, U, M, Q, W, Y and Z are as defined in the first aspect. These processes form further aspects of the invention.

Throughout the specification, general formulae are designated by Roman numerals I, II, III, IV etc. Subsets of these general formulae are defined as Ia, Ib, Ic etc, ... IVa, IVb, IVc etc.

The present invention covers a process for the preparation of a compound of formula (I) as hereinbefore defined, which comprises reductively aminating a compound of formula (II)

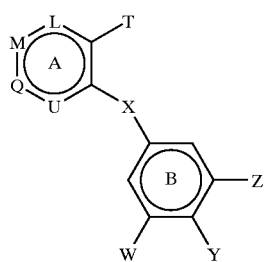

(II)

wherein L, M, Q, U, X, W, Y and Z are as hereinbefore defined and T is —CHO, with an amine of formula $NHR^1R^2$ wherein $R^1$, $R^2$ are as hereinbefore defined.

Preferably, the reducing agent is a borohydride reducing agent.

A further aspect of the present invention is a process for the preparation of a compound of formula (I) as hereinbefore defined wherein $R^1$ and $R^2$ are hydrogen, which comprises reducing a compound of formula (II) as hereinbefore defined wherein T is —CN.

Preferably, the reducing agent is $BH_3$.THF or lithium aluminium hydride or hydrogen in the presence of a metal catalyst.

A further aspect of the present invention is a process for the preparation of a compound of formula (I) as hereinbefore defined which comprises reducing a compound of formula (II) as hereinbefore defined wherein T is —$CONR^1R^2$, and $R^1$ and $R^2$ are as hereinbefore defined.

Preferably, the reducing agent is $BH_3$.THF or lithium aluminium hydride.

A further aspect of the present invention is a compound of formula (II) as hereinbefore defined wherein T is —CHO, CN or $CONR^1R^2$, and $R^1$ and $R^2$ are as hereinbefore defined.

A further aspect of the present invention is a process for the preparation of a compound of formula (I) as hereinbefore defined which comprises converting one compound of formula (I) into another compound of formula (I) using conventional techniques generally known in the art.

A further aspect of the present invention is a process for the preparation of a compound of formula (I) as hereinbefore defined which comprises deprotecting a protected compound of formula (I) using conventional techniques generally known in the art.

Compounds of general formula I may be prepared from compounds of general formula II by a variety of methods (see Scheme 1)

Scheme 1

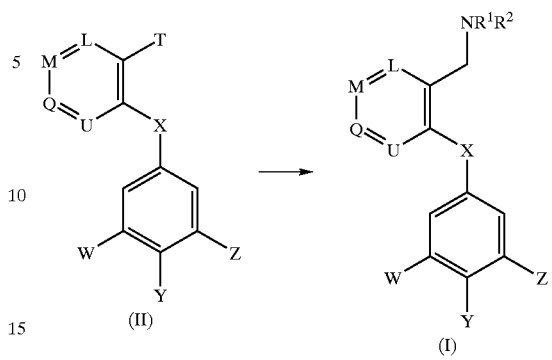

i) Compounds of general formula I may be prepared from compounds of general formula II where T is —CHO, by reaction with an amine of formula $HNR^1R^2$ (or a salt thereof), followed by reduction with a hydride reducing agent in a suitable solvent. When either $R^1$ or $R^2$ is hydrogen, suitable solvents include protic solvents such as ethanol, and sodium borohydride is an appropriate reducing agent. When neither $R^1$ or $R^2$ are hydrogen, tetrahydrofuran/dichloromethane is a suitable solvent system and sodium triacetoxyborohydride is a suitable reducing agent. In such reactions the use of a salt form of $HNR^1R^2$, such as the hydrochloride or acetate is preferable, and an auxiliary base, to aid solubility of the $HNR^1R^2$ salt, such as triethylamine may optionally be added along with acetic acid.

ii) Compounds of general formula I may be prepared from compounds of general formula II where T is cyano, by reduction to its corresponding amine of formula —$CH_2NH_2$, using hydride reducing agents such as $BH_3$.THF or lithium aluminium hydride or by hydrogenation with a suitable metal catalyst for example Raney Nickel.

iii) Compounds of general formula I may be prepared from compounds of general formula II where T is —$C(O)NR^1R^2$, by reduction to provide an amine, for example with a hydride reducing agent such as $BH_3$.THF or lithium aluminium hydride. Compounds of formula II where T is —$C(O)NR^1R^2$ may be prepared from the corresponding compounds of formula II where T is —$CO_2H$, by treatment with a coupling agent and an amine $HNR^1R^2$ in a suitable inert solvent which does not adversely affect the reaction. Compounds of formula II where T is —$CO_2H$ may themselves be formed from compounds of formula II where T is —CN or —$CO_2R^{10}$, and $R^{10}$=methyl or ethyl, by treatment with a suitable hydroxide salt in the presence of water and a suitable co-solvent at an appropriate temperature. Alternatively, Compounds of general formula II where T is —$C(O)NR^1R^2$ may be prepared from compounds of general formula II where T is —$CO_2R^{10}$ and $R^{10}$=methyl or ethyl, by reaction with an amine of general formula $NHR^1R^2$.

Alternatively, compounds of general formula I having a particular $NR^1R^2$ group may be converted into other compounds of general formula I having a different $NR^1R^2$ group. For example:

i) Compounds of formula I wherein $R^1$ or $R^2$ is hydrogen, can be converted into a compound of formula I wherein neither $R^1$ nor $R^2$ is hydrogen, by reaction with an aldehyde and a hydride reducing agent. Suitable aldehydes include formaldehyde, suitable reducing agents include sodium tri(acetoxy)borohydride and the reaction is preferably conducted in a solvent which does not interfere with the reaction, such as dichloromethane at or below room temperature.

ii) Compounds of formula I wherein $R^1$ or $R^2$ is hydrogen, can be converted into a compound of formula I wherein $R^1$ or $R^2$ is methyl, by reaction with a formylating agent, for example pentafluorophenyl formate, in a suitable solvent, followed by subsequent reduction of the intermediate N-formyl compound with a hydride reducing agent such as $BH_3$.THF or lithium aluminium hydride in an inert solvent, preferably at elevated temperature. Suitable formylating agents include pentafluorophenyl formate (formed from formic acid, pentafluorophenol and dicyclohexylcarbodiimide) and suitable solvents for the formylation include dichloromethane. Suitable reducing agents include borane-tetrahydrofuran complex and suitable inert solvents for the reduction include tetrahydrofuran.

Compounds of formula I where M or Q is —C($R^4$)— may be prepared from the corresponding halo compound by a variety of methods:

i) Compounds of formula I where M or Q is —C(CN)— may be prepared by reaction of the corresponding halo compound with a cyanide salt in the presence of a Pd(0) or (II)catalyst in a high boiling solvent at elevated temperatures. Suitable Pd catalysts include palladium tetrakis(triphenylphosphine), suitable cyanide salts include $Zn(CN)_2$ and suitable high boiling solvents which do not adversely affect the reaction include dimethylformamide.

ii) Compounds of formula I where M or Q is —C($CO_2R^9$)— may be prepared by reacting the corresponding halo compound with carbon monoxide at high pressure with a Pd(0) or (II) catalyst, in an alcohol solvent (ROH wherein R is $C_1$-$C_4$ alkyl), in the presence of a base at elevated temperatures.

Alternatively compounds of formula I where M or Q is —C($R^4$)— may be prepared from the corresponding compound of formula I where M or Q is —C($R^4$)— by a variety of methods.

i) Compounds of formula I where M or Q is —C($NH_2$)— may be prepared from the corresponding compounds of formula I where M or Q is —C($NO_2$)— by treatment with a reducing agent in a protic solvent at, or above, room temperature. Suitable reducing agents include iron powder/calcium chloride, suitable protic solvents include aqueous ethanol or acetic acid.

ii) Compounds of formula I where M or Q is —C($NHSO_2R^9$)— may be prepared from the corresponding compounds of formula I where M or Q is —C($NH_2$)— by reaction with a sulfonylating agent in the presence of a base in an inert solvent which does not adversely affect the reaction at, or below, room temperature. Suitable sulfonylating agents include methanesulfonyl chloride, suitable bases include triethylamine and suitable inert solvents include dichloromethane.

iii) Compounds of formula I where M or Q is —C($NR^8SO_2R^9$)— may be prepared from the corresponding compounds of formula I where M or Q is —C($NHSO_2R^9$)—, by treatment with an alkylating agent and a base in a suitable inert solvent. Examples of suitable alkylating agents include methyl iodide, suitable bases include potassium carbonate and suitable inert solvents include acetonitrile.

iv) Compounds of formula I where M or Q is —C(C(=O)$NH_2$)— may be prepared from the corresponding compounds of formula I where M or Q is —C(CN)—, by hydrolysis under basic, oxidative or acid conditions. Basic hydrolysis is preferably conducted with a hydroxide salt such as potassium hydroxide in a protic solvent such as t-butanol at elevated temperatures.

v) Compounds of formula I where M or Q is —C($CH_2OH$)— may be prepared from the corresponding compounds of formula I where M or Q is —C($CO_2R^{10}$)—, by treatment with a hydride reducing agent, such as lithium aluminium hydride.

vi) Compounds of formula I where M or Q is —C($CO_2H$)— may be prepared from the corresponding compounds of formula I where M or Q is —C($CO_2R^9$)—, by treatment with a suitable hydroxide salt in the presence of water and a suitable co-solvent.

vii) Compounds of formula I where M or O is —C($CONR^6R^7$)— may be prepared from the corresponding compounds of formula I where M or Q is —C($CO_2H$)—, by treatment with a coupling agent, a base and an amine $HNR^6R^7$ in a suitable inert solvent which does not adversely affect the reaction.

viii) Compounds of formula I where M or Q is —C($CO_2H$)— may be prepared from the corresponding compounds of formula I where M or Q is —C(Me)—, by treatment with a suitable oxidising agent in a suitable solvent which does not adversely affect the reaction.

Compounds of formula IIa, where X=S, may be prepared in turn from the coupling of compounds of general formula IV with compounds of general formula III, wherein LG is a suitable leaving group such as halogen (F, Cl, Br or I) or a sulfonate ester such as trifluoromethanesulfonate or methanesulfonate (preferably LG is F or Cl) (See Scheme 2). Such coupling reactions may be accomplished by techniques known in the art, such as via reaction with potassium carbonate in a suitable solvent such as dimethylformamide under appropriate reaction conditions such as elevated temperature and in an inert atmosphere.

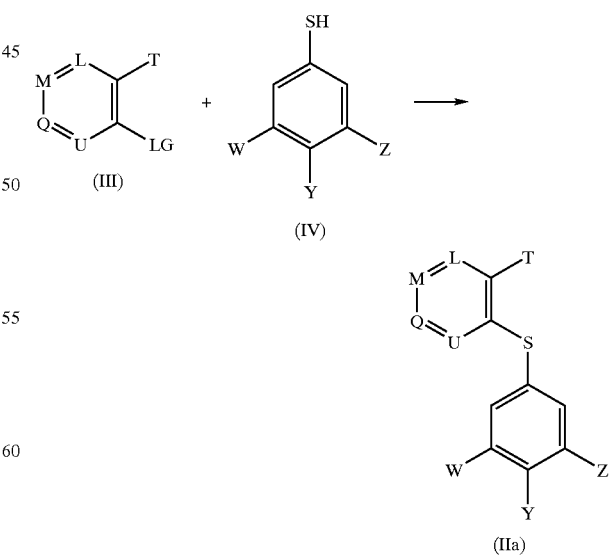

Scheme 2

Compounds of formula IIb, where X=—$CH_2$—, may be prepared in turn from the coupling of compounds of general formula V, wherein Hal is a halogen such as Br or Cl (preferably Hal is Br) with compounds of general formula III, wherein LG is a suitable leaving group such as halogen (F, Cl, Br or I) or a sulfonate ester such as trifluoromethanesulfonate or methanesulfonate (preferably LG is Cl) (See Scheme 3). Such coupling reactions may be accomplished by techniques known in the art, such as via reaction of V with a suitable form of Zinc metal, such as Riecke® Zinc, in a suitable solvent, such as tetrahydrofuran, followed by reaction of the resulting zincate with III in the presence of a suitable catalyst, such as bis(triphenylphosphine)nickel (II) chloride, under appropriate reaction conditions such as under an inert atmosphere.

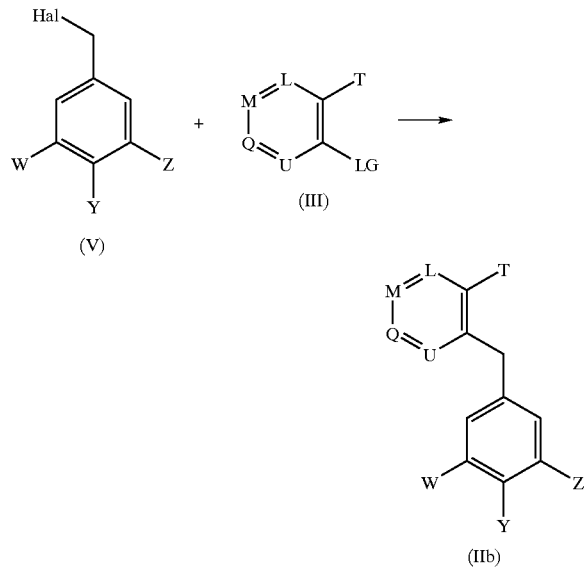

Scheme 3

Many compounds of formula IV and V are either known and available from commercial sources or are available from commercially available materials using known techniques Compounds of formula III are either known and available from commercial sources or are available from commercially available materials using known techniques (see Examples hereinafter). In particular compounds of formula III where M or Q are —C(R$^4$)— may be prepared from the corresponding halo compound, in analogous fashion to the methods described above to prepare compounds of formula I. Alternatively compounds of formula III where M or Q are —C(R$^4$)— may be prepared from the corresponding compound of formula III, in analogous fashion to the methods described above to prepare compounds of formula I.

The skilled person will appreciate that in appropriate cases introduction/elaboration of R$^4$ can be performed prior to conversion of T to —CH$_2$NR$^1$R$^2$.

Further, the skilled person will appreciate that the sulfide or zincate coupling (see schemes 2 and 3) may be performed after conversion of the group T to the group —CH$_2$NR$^1$R$^2$.

It will be apparent to those skilled in the art that sensitive functional groups may need to be protected and deprotected during synthesis of a compound of formula I. This may be achieved by conventional techniques, for example as described in 'Protective Groups in Organic Synthesis', 3rd edition, by T W Greene and P G M Wuts, John Wiley and Sons Inc, 1999.

The compounds of the invention are useful because they have pharmacological activity in mammals, including humans. More particularly, they are useful in the treatment or prevention of a disorder in which the regulation of monoamine transporter function is implicated. Disease states that may be mentioned include hypertension, depression (including depression in cancer patients, depression in Parkinson's patients, postmyocardial infarction depression, subsyndromal symptomatic depression, depression in infertile women, paediatric depression, major depression, single episode depression, recurrent depression, child abuse induced depression, post partum depression and grumpy old man syndrome), generalized anxiety disorder, phobias (including agoraphobia, social phobia and simple phobias), posttraumatic stress syndrome, avoidant personality disorder, sexual dysfunction (including premature ejaculation and male impotence), eating disorders (including anorexia nervosa and bulimia nervosa), obesity, substance abuse disorders (including chemical dependencies such as addictions to alcohol, cocaine, heroin, phenobarbital, nicotine and benzodiazepines), cluster headache, migraine, pain, Alzheimer's disease, obsessive-compulsive disorder, panic disorder, memory disorders (including dementia, amnestic disorders, and age-related cognitive decline (ARCD)), Parkinson's diseases (including dementia in Parkinson's disease, neuroleptic-induced parkinsonism and tardive dyskinesias), endocrine disorders (including hyperprolactinaemia), vasospasm (particularly in the cerebral vasculature), cerebellar ataxia, gastrointestinal tract disorders (involving changes in motility and secretion), negative symptoms of schizophrenia, premenstrual syndrome, fibromyalgia syndrome, stress incontinence, Tourette's syndrome, trichotillomania, kleptomania, attention deficit hyperactivity disorder (ADHD), chronic paroxysmal hemicrania, headache (associated with vascular disorders), emotional lability, pathological crying, sleeping disorder (cataplexy) and shock.

Disorders of particular interest include depression, attention deficit hyperactivity disorder, obsessive-compulsive disorder, post-traumatic stress syndrome, substance abuse disorders and sexual dysfunction including male impotence and (in particular) premature ejaculation. Premature ejaculation may be defined as persistent or recurrent ejaculation before, upon or shortly after penile penetration of a sexual partner. It may also be defined as ejaculation occurring before the individual wishes [see 'The Merck Manual', 16$^{th}$ edition, p 1576, published by Merck Research Laboratories, 1992].

Thus, according to further aspects, the invention provides:
  i) A compound of formula (I), as defined in the first aspect, pharmaceutically acceptable salts, solvates or polymorphs thereof, for use as a medicament.
  ii) The use of a compound of formula (I), as defined in the first aspect, pharmaceutically acceptable salts, solvates or polymorphs thereof, in the preparation of a medicament for the treatment or prevention of a disorder in which the regulation of monoamine transporter function is implicated, for example hypertension, depression, generalized anxiety disorder, phobias, post-traumatic stress syndrome, avoidant personality disorder, sexual dysfunction (e.g. premature ejaculation and male impotence), eating disorders, obesity, substance abuse disorders (e.g. chemical dependencies such as addictions to alcohol, cocaine, heroin, phenobarbital, nicotine and benzodiazepines), cluster headache, migraine, pain, Alzheimer's disease, obsessive-compulsive disorder, panic disorder, memory disorders, Parkinson's diseases, endocrine disorders, vasospasm, cerebellar ataxia, gastrointestinal tract disorders, negative symptoms of schizophrenia, premenstrual syndrome, fibromyalgia syndrome, stress incontinence, Tourette's syndrome, trichotillomania, kleptomania, attention deficit hyperactivity disorder (ADHD), chronic paroxysmal hemicrania, headache (associated with vascular disorders), emotional lability, pathological crying, sleeping disorder (cataplexy) and shock.

iii) The use of a compound of formula (I), as defined in the first aspect, pharmaceutically acceptable salts, solvates or polymorphs thereof, in the preparation of a medicament for the treatment or prevention of a disorder in which the regulation of monoamine transporter function is implicated where that disorder is depression, attention deficit hyperactivity disorder, obsessive-compulsive disorder, post-traumatic stress syndrome, substance abuse disorders or sexual dysfunction (e.g. premature ejaculation and male impotence).

iv) The use of a compound of general formula (I) as defined in the first aspect, pharmaceutically acceptable salts, solvates or polymorphs thereof, in the manufacture of a medicament for the treatment or prevention of premature ejaculation, and also provides a method of treatment or prevention of premature ejaculation comprising the administration of this compound to a patient in need of such treatment or prevention.

v) A method of treatment or prevention of depression, attention deficit hyperactivity disorder, obsessive-compulsive disorder, post-traumatic stress syndrome, substance abuse disorders and sexual dysfunction including male impotence and (in particular) premature ejaculation, which comprises administering a therapeutically effective amount of a compound of formula (I) as defined in the first aspect, pharmaceutically acceptable salts, solvates or polymorphs thereof, to a patient in need of such treatment or prevention.

vi) A method of increasing ejaculatory latency which comprises the administration of an effective amount of a compound of formula (I) as defined in the first aspect, pharmaceutically acceptable salts, solvates or polymorphs thereof, to a male desiring increased ejaculatory latency.

vii) A compound of formula (I) as defined in the first aspect, pharmaceutically acceptable salts, solvates or polymorphs thereof, for the treatment or prevention of a disorder in which the regulation of monoamine transporter function is implicated, for example depression, attention deficit hyperactivity disorder, obsessive-compulsive disorder, post-traumatic stress syndrome, substance abuse disorders and sexual dysfunction including male impotence and (in particular) premature ejaculation.

It is to be appreciated that all references herein to treatment include curative, palliative and prophylactic treatment.

The compounds of the invention may be administered alone or as part of a combination therapy. If a combination of active agents are administered, then they may be administered simultaneously, separately or sequentially. In particular, the compounds of the invention may be combined with the following for the treatment of PE:

Alpha-blockers (e.g. phentolamine, doxazasim, tansulosin, terazasin, prazasin and Example 19 of WO9830560;

Apomorphine—teachings on the use of apomorphine as a pharmaceutical may be found in U.S. Pat. No. 5,945,117;

Dopamine D2 agonists (e.g. Premiprixal, Pharmacia Upjohn compound number PNU95666);

Melanocortin receptor agonists (e.g. Melanotan II);

PGE1 receptor agonists (e.g. alprostadil);

Mono amine transport inhibitors, particularly Noradrenaline Re-uptake Inhibitors (NRIs) (e.g. Reboxetine), other Serotonin Re-uptake Inhibitors (SRIs) (e.g. paroxetine) or Dopamine Re-uptake Inhibitors (DRIs);

5-$HT_{1A}$ antagonists (e.g. robalzotan)

5-HT3 antagonists (e.g. ondansetron and granisetron); and

PDE inhibitors such as PDE2 (e.g. erythro-9-(2-hydroxyl-3-nonyl)-adenine) and Example 100 of EP 0771799-incorporated herein by reference) and in particular a PDE5 inhibitor (e.g. sildenafil, 1-{([3-(3,4-dihydro-5-methyl-4-oxo-7-propylimidazo[5,1-f]-as-trazin-2-yl)-4-ethoxyphenyl]sulfonyl}-4-ethylpiperazine i.e. vardenafil/Bayer BA 38-9456 or IC351 (see structure below, Icos Lilly)).

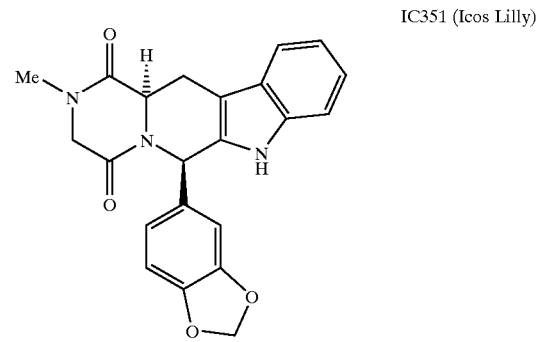

IC351 (Icos Lilly)

For human use the compounds of the invention can be administered alone but in human therapy will generally be administered in admixture with a suitable pharmaceutical excipient, diluent or carrier selected with regard to the intended route of administration and standard pharmaceutical practice. Accordingly the present invention provides for a composition comprising a compound of formula (I) as disclosed herein, or pharmaceutically acceptable salts, solvates or polymorphs thereof, and a pharmaceutically acceptable diluent or carrier.

For example, the compounds of the invention, can be administered orally, buccally or sublingually in the form of tablets, capsules (including soft gel capsules), ovules, elixirs, solutions or suspensions, which may contain flavouring or colouring agents, for immediate-, delayed-, modified-, sustained-, dual-, controlled-release or pulsatile delivery applications. The compounds of the invention may also be administered via intracavernosal injection. The compounds of the invention may also be administered via fast dispersing or fast dissolving dosage forms.

Such tablets may contain excipients such as microcrystalline cellulose, lactose, sodium citrate, calcium carbonate, dibasic calcium phosphate, glycine, and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia.

Additionally, lubricating agents such as magnesium stearate stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention, and their pharmaceutically acceptable salts, may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients may be present both within the dosage form i.e. within the matrix, and/or on the dosage form, i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The compounds of the invention can also be administered parenterally, for example, intravenously, intra-arterially, intraperitoneally, intrathecally, intraventricularly, intraurethrally, intrasternally, intracranially, intramuscularly or subcutaneously, or they may be administered by infusion techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The following dosage levels and other dosage levels herein are for the average human subject having a weight range of about 65 to 70 kg. The skilled person will readily be able to determine the dosage levels required for a subject whose weight falls outside this range, such as children and the elderly.

For oral and parenteral administration to human patients, the daily dosage level of the compounds of the invention or salts or solvates thereof will usually be from 10 to 500 mg (in single or divided doses).

Thus, for example, tablets or capsules of the compounds of the invention or salts or solvates thereof may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case.

There can, of course, be individual instances where higher or lower dosage ranges are merited and such are within the scope of this invention. The skilled person will also appreciate that, in the treatment of certain conditions (including PE), compounds of the invention may be taken as a single dose on an "as required" basis (i.e. as needed or desired).

Example Tablet Formulation

In general a tablet formulation could typically contain between about 0.01 mg and 500 mg of a compound according to the present invention (or a salt thereof) whilst tablet fill weights may range from 50 mg to 100 mg. An example formulation for a 10 mg tablet is illustrated:

| Ingredient | % w/w |
| --- | --- |
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The compounds of the invention can also be administered intranasally or by inhalation and are conveniently delivered in the form of a dry powder inhaler or an aerosol spray presentation from a pressurised container, pump, spray or nebulizer with the use of a suitable propellant, e.g. dichlorodifluoromethane, trichlorofluoromethane, dichlorotetra-fluoro-ethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebulizer may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a compound of the invention for delivery to the patient. The overall daily dose with an aerosol will be in the range of from 1 to 50 mg which may be administered in a single dose or, more usually, in divided doses throughout the day.

The compounds of the invention may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the compounds of the invention can be administered in the form of a suppository or pessary, or they may be applied topically in the form of a gel, hydrogel, lotion, solution, cream, ointment or dusting powder. The compounds of the invention may also be dermally or transdermally administered, for example, by the use of a skin patch. They may also be administered by the ocular, pulmonary or rectal routes.

For ophthalmic use, the compounds can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters, wax, cetearyl alcohol, 2-octyldodecanol, benzyl alcohol and water.

The compounds of the invention may also be used in combination with a cyclodextrin. Cyclodextrins are known to form inclusion and non-inclusion complexes with drug molecules. Formation of a drug-cyclodextrin complex may modify the solubility, dissolution rate, bioavailability, and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

For oral or parenteral administration to human patients the daily dosage levels of the compounds of the invention will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The physician will in any event determine the actual dosage which will be most suitable for any particular patient and it will vary with the age, weight and response of the particular patient. The above dosages are, of course only exemplary of the average case and there may be instances where higher or lower doses are merited, and such are within the scope of the invention.

Oral administration is preferred. Preferably, administration takes place shortly before an effect is required.

For veterinary use, a compound of the invention, or a veterinarily acceptable salt thereof, or a veterinarily acceptable solvate or pro-drug thereof, is administered as a suitably acceptable formulation in accordance with normal veterinary practice and the veterinary surgeon will determine the dosing regimen and route of administration which will be most appropriate for a particular animal.

Thus according to a further aspect, the invention provides a pharmaceutical formulation containing a compound of formula (I), as defined in the first aspect, or a pharmaceutically acceptable salt thereof, and a pharmaceutically acceptable adjuvant, diluent or carrier.

The invention is illustrated by the following non-limiting examples in which the following abbreviations and definitions are used:

| DMF | N,N-dimethylformamide |
| DMSO | dimethylsulfoxide |
| Ex | Example |
| ES$^+$ | electrospray ionisation positive scan |
| ES$^-$ | electrospray ionisation negative scan |
| h | hours |
| m/z | mass spectrum peak |
| min | minutes |
| MS | mass spectrum |
| Prec | Precursor |
| Prep | Preparation |
| THF | tetrahydrofuran |
| TS$^+$ | thermospray ionisation positive scan |

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks; e.g. s, singlet; d, doublet; t, triplet; q, quartet; m, multiplet; br, broad. Where thin layer chromatography (TLC) has been used it refers to silica gel TLC using silica gel 60 F$_{254}$ plates.

EXAMPLE 1

N-Methyl-N-[(4-{[4-(methylsulfanyl)phenyl]sulfanyl}-3-pyridinyl)methyl]amine

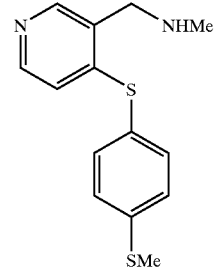

The aldehyde of Preparation 1 (from 3.5 mmol of 4-chloronicotinaldehyde) was dissolved in an 8M solution of methylamine in EtOH (9 mL, 72 mmol) and the mixture was stirred at room temperature for 1 h. NaBH$_4$ (190 mg, 5.0 mmol) was added in one portion and stirring was continued overnight. The reaction was quenched by the cautious addition of 2M HCl (20 mL) and stirred for 1 h before being basified to pH 10 with 10% aqueous K$_2$CO$_3$. The mixture was extracted with EtOAc (200 mL) and the organic layer was dried (MgSO$_4$) and evaporated. Purification of the residue by column chromatography [SiO$_2$; CH$_2$Cl$_2$ increasing polarity to 10% (9:1, MeOH:NH$_4$OH) in CH$_2$Cl$_2$] gave (4-{[4-(methylsulfanyl)phenyl]sulfanyl}-3-pyridinyl)methanol (608 mg, 66%) and the title amine (133 mg, 14%) as a colourless oil. A sample of the title amine was taken up in CH$_2$Cl$_2$ and treated with 1M ethereal HCl. Removal of the solvent then gave the bis HCl salt as a white solid; δ$_H$ (CD$_3$OD, 400 MHz) 2.56 (3H, s), 2.93 (3H, s), 4.58 (2H, s), 7.22 (1H, d), 7.50 (2H, d), 7.61 (2H, d), 8.47 (1H, d), 8.84 (1H, s); MS m/z (ES$^-$) 347 (M+2HCl−H$^+$).

EXAMPLE 2

N,N-Dimethyl-N-[(4-{[4-(methylsulfanyl)phenyl]sulfanyl}-3-pyridinyl)methyl]amine

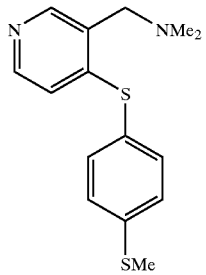

Formaldehyde (100 μL, 1.23 mmol) was added to a solution of the amine of Example 1 (112 mg, 0.41 mmol) in CH$_2$Cl$_2$ (4 mL) and the mixture was stirred at room temperature for 15 min before the addition of sodium triacetoxyborohydride (348 mg, 1.64 mmol). The reaction was stirred a further 16 h at room temperature and then partitioned between 10% aqueous K$_2$CO$_3$ (30 mL) and EtOAc (50 mL). The organic layer was dried (MgSO$_4$) and evaporated and the residue was taken up in CH$_2$Cl$_2$ and treated with 1M ethereal HCl to give the bis HCl salt of the title amine (142 mg, 96%) as a white solid; $\delta_H$ (CD$_3$OD, 400 MHz) 2.56 (3H, s), 3.07 (6H, s), 4.72 (2H, s), 7.22 (1H, d), 7.51 (2H, d), 7.62 (2H, d), 8.49 (1H, d), 8.96 (1H, s); MS m/z (ES$^+$) 291 (MH$^+$).

EXAMPLE 3

N-Methyl-N-[(3-{[4-(methylsulfanyl)phenyl]sulfanyl}-4-pyridinyl)methyl]amine

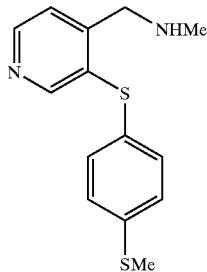

Ti(O$^i$Pr)$_4$ (2 mL, 6.77 mmol) was added to a solution of the aldehyde of Preparation 2 (from 3.9 mmol of 3-chloroisonicotinaldehyde) in an 8M solution of methylamine in EtOH (5 mL, 40 mmol) and the mixture was stirred at room temperature for 3 h. NaBH$_4$ (200 mg, 5.3 mmol) was added in one portion and stirring was continued overnight. The reaction was quenched by the cautious addition of 2M HCl (20 mL) and stirred for 1 h before being basified to pH 10 with 10% aqueous K$_2$CO$_3$. The mixture was extracted with EtOAc (2×50 mL) and the combined organic layers were washed with brine, dried (MgSO$_4$) and evaporated. The residue was taken up in EtOAc (10 mL) and 1M ethereal HCl (~10 mL) was added to precipitate the bis HCl salt. The resulting suspension was stirred for 1 h and then filtered and dried in vacuo, to give the bis HCl salt of the title compound (1.08 g, 79%) as a pale yellow powder; $\delta_H$ (CD$_3$OD, 300 MHz) 2.53 (3H, s), 2.93 (3H, s), 4.56 (2H, s), 7.19 (2H, d), 7.49 (2H, d), 7.88 (1H, d), 8.36 (1H, s), 8.70 (1H, d); MS m/z (ES$^+$) 277 (MH$^+$).

EXAMPLE 4

N,N-Dimethyl-N-[(3-{[4-(methylsulfanyl)phenyl]sulfanyl}-4-pyridinyl)methyl]amine

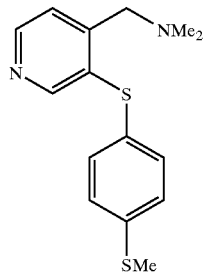

The title compound was prepared by the method of Example 2, starting from the secondary amine of Example 3. Bis HCl salt: $\delta_H$ (CD$_3$OD, 300 MHz) 2.52 (3H, s), 3.04 (6H, s), 4.70 (2H, s), 7.39 (2H, d), 7.46 (2H, d), 7.99 (1H, d), 8.39 (1H, s), 8.70 (1H, d); MS m/z (ES$^+$) 291 (MH$^+$).

EXAMPLE 5

N-methyl-N-({3-[4-(methylsulfanyl)benzyl]-4-pyridinyl}methyl)amine

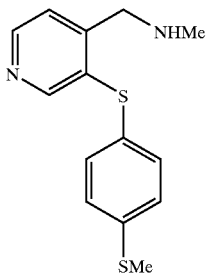

BH$_3$.THF (1M soln in THF, 10.7 ml, 10.7 mmol) was added to a solution of the amide of Preparation 5 (970 mg, 3.57 mmol) in THF (5 ml) under nitrogen and the mixture was heated at reflux for 2 h. After cooling to room temperature the rreaction was cautiously quenched by the addition of 6M HCl (10 mL) and the resulting mixture was heated at reflux for 2 h. After cooling to room temperature the mixture was concentrated in vacuo to remove THF and the yellow solution was washed with ether (10 mL). The aqueous layer was basified with conc. NH$_3$ (aq) and extracted with CH$_2$Cl$_2$ (5×10 mL). The combined CH$_2$Cl$_2$ extracts were dried (MgSO$_4$) and evaporated to an oil. The residue was purified by column chromatography [SiO$_2$; CH$_2$Cl$_2$:MeOH:NH$_4$OH, 95:5:0.5] to give the title compound (768 mg, 83%) as a colourless oil. A sample was taken up in CH$_2$Cl$_2$ and treated with 1M ethereal HCl to give the bis HCl salt of the title amine as a white powder; $\delta_H$ (CD$_3$OD, 400 MHz) 2.47 (3H, s), 2.87 (3H, s), 4.32 (2H, s), 4.55 (2H, s), 7.19 (2H, d), 7.28 (2H, d), 8.13 (1H, d), 8.61 (1H, s), 8.88 (1H, d); MS m/z (TS$^+$) 259 (MH$^+$).

EXAMPLE 6

N,N-dimethyl-N-({3-[4-(methylsulfanyl)benzyl]-4-pyridinyl}methyl)amine

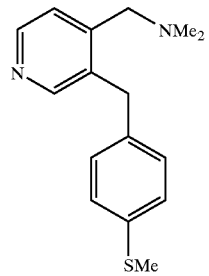

The title compound was prepared by the method of Example 2, starting from the secondary amine of Example 5. Bis HCl salt: $\delta_H$ (CD$_3$OD, 400 MHz) 2.47 (3H, s), 2.96 (6H, s), 4.38 (2H, s), 4.71 (2H, s), 7.20 (2H, d), 7.29 (2H, d), 8.37 (1H, d), 8.65 (1H, s), 8.89 (1H, d); MS m/z (TS$^+$) 273 (MH$^+$).

EXAMPLE 7

N-methyl-N-({4-[4-(methylsulfanyl)benzyl]-3-pyridinyl}methyl)amine

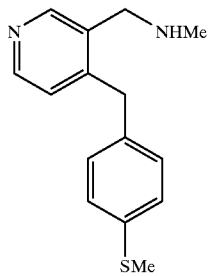

The title compound was prepared by the method of Example 5, starting from the amide of Preparation 7. Bis HCl salt: $\delta_H$ (CD$_3$OD, 400 MHz) 2.48 (3H, s), 2.89 (3H, s), 4.44 (2H, s), 4.57 (2H, s), 7.21 (2H, d), 7.30 (2h, d), 7.72 (1H, d), 8.78 (1H, d), 9.02 (1H, s); MS m/z (TS$^+$) 259 (MH$^+$).

EXAMPLE 8

N,N-dimethyl-N-({4-[4-(methylsulfanyl)benzyl]-3-pyridinyl}methyl)amine

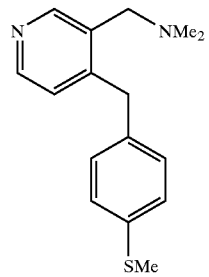

The title compound was prepared by the method of Example 2, starting from the secondary amine of Example 7. Bis HCl salt: $\delta_H$ (CD$_3$OD, 400 MHz) 2.46 (3H, s), 2.99 (6H, s), 4.47 (2H, s), 4.74 (2H, s), 7.21 (2H, d), 7.30 (2H, d), 7.74 (1H, d), 8.78 (1H, d), 9.15 (1H, s); MS m/z (TS$^+$) 273 (MH$^+$).

Preparations

Preparation 1

4-{[4-(Methylsulfanyl)phenyl]sulfanyl}nicotinaldehyde

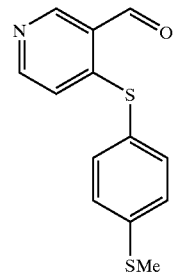

4-Chloronicotinaldehyde [prepared according to D. Albanese, M. Penso, M. Zenoni, Synthesis 1999, 1294–1296] (500 mg, 3.5 mmol), 4-methylsulfanyl-benzenethiol (606 mg, 3.88 mmol) potassium carbonate (586 mg, 4.24 mmol) and DMF (7 mL) were combined, the mixture was heated together at 50° C. for 1.5 h and then stirred at room temperature overnight. The solvent was removed in vacuo and the residue was partitioned between EtOAc (100 mL) and 10% aqueous K$_2$CO$_3$ (100 mL). The organic layer was dried (MgSO$_4$) and evaporated to give the title compound (1.05 g) as a yellow oil. The $^1$H NMR spectrum showed the material to be of sufficient purity (90–95%) to be used without further purification; $\delta_H$ (CDCl$_3$, 400 MHz) 2.54 (3H, s), 6.69 (1H, d), 7.35 (2H, d), 7.4 (2H, d), 8.35 (1H, d), 8.87 (1H, s), 10.24 (1H, s); MS m/z (TS$^+$) 262 (MH$^+$).

Preparation 2

3-{[4-(Methylsulfanyl)phenyl]sulfanyl}isonicotinaldehyde

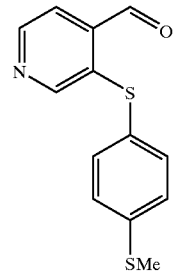

3-Chloroisonicotinaldehyde [prepared according to R. B. Moffett et al., J. Heterocycl. Chem. 1979, 16, 1459] (550 mg, 3.9 mmol), 4-methylsulfanyl-benzenethiol (732 mg, 4.7 mmol) potassium carbonate (700 mg, 5.1 mmol) and DMF (10 mL) were combined and the mixture was heated together at 65° C. for 2 h. The solvent was removed in vacuo and the residue was partitioned between EtOAc (50 mL) and water (50 mL). The organic layer was washed with brine, dried (MgSO$_4$) and evaporated to give the title compound (1.124 g) as a yellow oil. The $^1$H NMR spectrum showed the material to be of sufficient purity (90–95%) to be used without further purification; $\delta_H$ (CDCl$_3$, 300 MHz) 2.52 (3H, s), 7.28 (2H, d), 7.40 (2H, d), 7.64 (1H, d), 8.39 (1H, s), 8.61 (1H, d), 10.42 (1H, s); MS m/z (ES$^-$) 260 (M–H$^+$).

Preparation 3

Methyl 3-[4-(methylsulfanyl)benzyl]isonicotinate

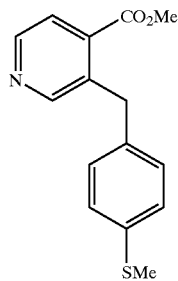

A solution of 1-(bromomethyl)-4-(methylsulfanyl) benzene (prepared according to D. D. M. Wayner, D. R. Arnold, *Can J. Chem.*, 1984, 62, 1164) (2.54 g, 11.7 mmol) in THF (10 mL) was added dropwise to a slurry of Riecke® Zinc in THF (22.8 mL of a commercial suspension [5 g Zn/100 mL], 17.5 mmol) under nitrogen. During this time the temperature rose steadily to 35° C. After allowing the black slurry to cool to room temperature over 30 min bis(triphenylphosphine)nickel (II) chloride (762 mg, 1.17 mmol) was added followed by a solution of methyl 3-chloroisonicotinate (prepared according to J. Epsztajn, M. W. Plotka, A. Grabowska, *Synth. Commun.*, 1997, 27, 1075) (1.0 g, 5.83 mmol) in THF (10 mL), dropwise, taking care to keep the temperature below 30° C. After the addition was complete the reaction was allowed to cool to room temperature over 1 h before being quenched by the addition of sat. NH$_4$Cl (aq) (20 mL) while cooling with an ice bath. The mixture was filtered through Celite®, washing well with EtOAc (3×20 mL), the organic layer was separated, dried (MgSO$_4$) and evaporated to give a brown oil. The residue was purified by column chromatography [SiO$_2$; EtOAc:pentane, 1:3 increasing polarity to EtOAc:pentane, 1:1 and then to (EtOAc:MeOH:NH$_4$OH, 95:5:0.5):pentane, 1:1] to give the title compound as an orange oil; $\delta_H$ (CDCl$_3$, 400 MHz) 2.43 (3H, s), 3.82 (3H, s), 4.30 (2H, s), 7.05 (2H, d), 7.18 (2H, d), 7.67 (1H, br), 8.59 (2H, br); MS m/z (TS$^+$) 274 (MH$^+$).

Preparation 4

3-[4-(methylsulfanyl)benzyl]isonicotinic acid

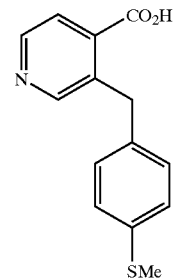

The ester of Preparation 3 (1.50 g, 5.5 mmol) was combined with NaOH (1.10 g, 27.5 mmol), water (6.5 mL) and MeOH (13 mL) and the mixture was heated at reflux for 2 h. After cooling in an ice bath the mixture was acidified with conc. HCl and the resulting yellow suspension was concentrated in vacuo to remove MeOH before being filtered and washed with ice water (3×5 mL). After drying in vacuo this gave the title acid (1.31 g, 81%) as a pale green solid; $\delta_H$ (DMSO, 300 MHz) 2.42 (3H, s), 4.27 (2H, s), 7.10 (2H, d), 7.15 (2H, d), 7.62 (1H, d), 8.58 (1H, d), 8.61 (1H, s), 13.6 (1H, br); MS m/z (TS$^+$) 260 (MH$^+$).

Preparation 5

N-methyl-3-[4-(methylsulfanyl)benzyl] isonicotinamide

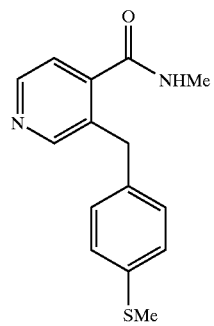

Oxalyl chloride (575 µL, 6.6 mmol) was added to a suspension of the acid of Preparation 4 (1.3 g, 4.4 mmol) in CH$_2$Cl$_2$ (10 mL) containing 2 drops of DMF. The mixture was stirred at room temperature for 1.5 h then evaporated to dryness, suspended in CH$_2$Cl$_2$ (10 mL) and re-evaporated. The residue was re-suspended in CH$_2$Cl$_2$ (10 mL) and treated with triethylamine (1.84 mL, 13.2 mmol) followed by a 2M solution of methylamine in THF (3.3 mL, 6.6 mmol). The resulting brown mixture was stirred at room temperature for 1 h before the addition of sat. NaHCO$_3$ (aq) (20 mL). The layers were separated, the aqueous layer was extracted with CH$_2$Cl$_2$ (4×20 mL) and the combined organic layers were dried (MgSO$_4$) and evaporated. The residue was purified by column chromatography [SiO$_2$; CH$_2$Cl$_2$:MeOH:NH$_4$OH, 96:4:0.4] to give the title compound (971 mg, 81%) as an off-white solid; $\delta_H$ (CDCl$_3$, 400 MHz) 2.40 (3H, s), 2.81 (3H, d), 4.07 (2H, s), 5.50 (1H, br), 7.04 (2H, br), 7.07–7.19 (3H, m), 8.50 (2H, m); MS m/z (TS$^+$) 273 (MH$^+$).

Preparation 6

4-chloro-N-methylnicotinamide

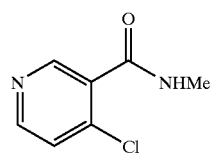

Oxalyl chloride (1.01 mL, 11.6 mmol) was added to a suspension of 4-chloronicotinic acid (prepared according to F. Guillier et al. *J. Org. Chem.* 1995, 60, 292) (1.5 g, 7.7 mmol) in CH$_2$Cl$_2$ (15 mL) containing 2 drops of DMF. The mixture was stirred at room temperature for 1 h then evaporated to dryness, suspended in CH$_2$Cl$_2$ (10 mL) and re-evaporated. The residue was re-suspended in CH$_2$Cl$_2$ (10 mL), cooled to 0° C. and treated with triethylamine (3.23 mL, 23.2 mmol) dropwise followed by a 2M solution of methylamine in THF (7.7 mL, 15.4 mmol) dropwise. The resulting orange mixture was stirred at 0° C. for 20 min before being concentrated in vacuo. The residue was treated with sat. NaHCO$_3$ (aq) (30 mL), extracted with CH$_2$Cl$_2$ 10×25 mL) and the combined organic layers were dried (MgSO$_4$) and evaporated to give an orange oil which crystallised. The solid was triturated with ether (10 mL), stirred for 30 min, then filtered and washed with 1:1 ether/pentane (20 mL) to give the title amide (986 mg, 75%) as an off-white solid; $\delta_H$ (CDCl$_3$, 400 MHz) 3.07 (3H, d), 6.20 (1H, br), 7.37 (1H, d), 8.53 (1H, d), 8.86 (1H, s).

Preparation 7

N-methyl-4-[4-(methylsulfanyl)benzyl]nicotinamide

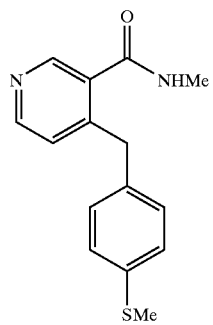

The title compound was prepared by the method of Preparation 3, using 4-chloro-N-methylnicotinamide instead of methyl 3-chloroisonicotinate. This gave the title amide as a pale brown solid; $\delta_H$(CDCl$_3$, 400 MHz) 2.47 (3H, s), 2.93 (3H, d), 4.13 (2H, s), 5.75 (1H, br), 7.08–7.16 (3H, m), 7.19 (2H, d), 8.45–8.60 (2H, br); MS m/z (TS$^+$) 273 (MH$^+$).

Biological Activity

A number of compounds were tested for biological activity by their ability to inhibit the uptake of serotonin by human serotonin transporters as follows.
(i) Cell Culture Human embryonic kidney cells (HEK-293) stably transfected with either the human serotonin transporter (hSERT), noradrenaline transporter (hNET) or dopamine transporter (hDAT) were cultured under standard cell culture techniques (cells were grown at 37° C. and 5% CO$_2$ in DMEM-culture media (supplemented with 10% dialysed foetal calf serum (FCS), 2 mM I-glutamine and 250 μg/ml geneticin)). Cells were harvested for the assay to yield a cell suspension of 750,000 cells/ml.
(ii) Determination of Inhibitor Potency All test compounds were dissolved in 100% DMSO and diluted down in assay buffer to give appropriate test concentrations. Assays were carried out in 96-well filter bottom plates. Cells (7500 cells/assay well) were pre-incubated in standard assay buffer containing either test compound, standard inhibitor or compound vehicle (1% DMSO) for 5 minutes. Reactions were started by addition of either $^3$H-Serotonin, $^3$H-Noradrenaline or $^3$H-Dopamine substrates. All reactions were carried out at room temperature in a shaking incubator. Incubation times were 5 minutes for the hSERT and hDAT assays and 15 minutes for the hNET assay. Reactions were terminated by removal of the reaction mixture using a vacuum manifold followed by rapid washing with ice cold assay buffer. The quantity of $^3$H-substrate incorporated into the cells was then quantified.

Assay plates were dried in a microwave oven, scintillation fluid added, and radioactivity measured. Potency of test compounds was quantified as IC$_{50}$ values (concentration of test compound required to inhibit the specific uptake of radiolabelled substrate into the cells by 50%).

(iii) Standard Assay Buffer Composition

Trizma hydrochloride (26 mM)

NaCl (124 mM)

KCl (4.5 mM)

KH$_2$PO$_4$ (1.2 mM)

MgCl$_2$.6H$_2$O (1.3 mM)

Ascorbic acid (1.136 mM)

Glucose (5.55 mM)

pH 7.40

CaCl$_2$ (2.8 mM)

Pargyline (100 μM)

Note: The pH of the buffer was adjusted to 7.40 with 1M NaOH before addition of CaCl$_2$ and pargyline.

| (iv) Summary of Assay Parameters | | | |
|---|---|---|---|
| | hSERT Assay | hDAT Assay | hNET Assay |
| Cell concentration per assay well. | 75,000 | 75,000 | 75,000 |
| Substrate Concentration. | $^3$H-5HT (50 nM) | $^3$H-Dopamine (200 nM) | $^3$H-Noradrenaline (200 nM) |
| Incubation time (minutes) | 5 | 5 | 15 |

The compounds of the invention are potent and selective inhibitors of serotonin re-uptake and the compounds of Examples 1–8 have a serotonin re-uptake inhibition (SRI) IC$_{50}$ value of less than or equal to 25 nM and are more than 100-fold as potent in the inhibition of serotonin re-uptake than in the inhibition of dopamine re-uptake and noradrenaline re-uptake.

The following results were obtained for Example 2:

| Example No. | SRI (nM) | DRI (nM) | NRI (nM) |
|---|---|---|---|
| 2 | 2.2 | 11698 | 564 |

What is claimed is:

1. A compound of formula (I) or pharmaceutically acceptable salts, solvates or polymorphs thereof;

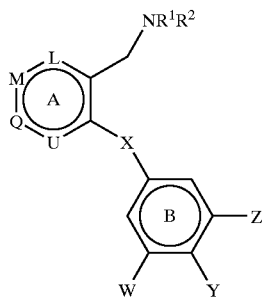

wherein;

X is S or $CH_2$;

L and U, which may be the same or different, are —N—, —$N^+$(—$O^-$)— or —C(H)—;

M and Q, which may be the same or different, are —N—, —$N^+$(—$O^-$)— or —C($R^4$)—;

wherein ring A contains 1 or 2 nitrogen atoms, and wherein when L, U, M or Q is —$N^+$(—$O^-$)—, ring A contains no other nitrogen atom;

$R^1$ and $R^2$, which may be the same or different, are hydrogen, $C_1$–$C_6$alkyl, $(CH_2)_m(C_3$–$C_6$cycloalkyl) wherein m=0, 1, 2 or 3, or $R^1$ and $R^2$ together with the nitrogen to which they are attached form an azetidine ring;

W, Y and Z, which may be the same or different, are hydrogen, halogen, $C_1$–$C_6$alkyl, $CF_3$, $OCF_3$, $C_1$–$C_4$alkylthio or $C_1$–$C_4$alkoxy; or Y and Z are linked so that, together with the interconnecting atoms, Y and Z form a fused 5 to 7-membered carbocyclic or heterocyclic ring which may be saturated, unsaturated or aromatic, and wherein when Y and Z form a heterocyclic ring, in addition to carbon atoms, the linkage contains one or two heteroatoms independently selected from oxygen, sulfur and nitrogen; and wherein W, Y and Z are not all hydrogen; and each $R^4$ is independently:

—$(CH_2)_p$—$R^5$;

where p is 0, 1 or 2;

$R^5$ is hydrogen, $CONR^6R^7$, $SO_2NR^6R^7$, $SO_2NHC$(=O) $R^6$, hydroxy, $C_1$–$C_4$alkoxy, $NR^8SO_2R^9$, $NO_2$, $NR^6R^{11}$, CN, $CO_2R^{10}$, $SR^{10}$, $S(O)R^9$ or $SO_2R^{10}$; $R^6$, $R^7$, $R^8$ and $R^{10}$ which may be the same or different, are hydrogen or $C_1$–$C_6$alkyl optionally substituted independently by one or more $R^{12}$; $R^9$ is $C_1$–$C_6$ alkyl optionally substituted independently by one or more $R^{12}$; $R^{11}$ is hydrogen, $C_1$–$C_6$ alkyl optionally substituted independently by one or more $R^{12}$, $C(O)R^6$, $CO_2R^9$, $C(O)$ $NHR^6$ or $SO_2NR^6R^7$; $R^{12}$ is fluoro, hydroxy, $CO_2H$, $C_3$–$C_6$cycloalkyl, $NH_2$, $CONH_2$, $C_1$–$C_6$alkoxy, $C_1$–$C_6$alkoxycarbonyl or a 5- or 6-membered heterocyclic ring containing 1, 2 or 3 heteroatoms selected from N, S and O optionally substituted independently by one or more $R^{13}$; or $R^6$ and $R^7$, together with the nitrogen to which they are attached, form a 4-, 5- or 6-membered heterocyclic ring optionally substituted independently by one or more $R^{13}$; or a 5- or 6-membered heterocyclic ring containing 1, 2 or 3 heteroatoms selected from N, S and O, optionally substituted independently by one or more $R^{13}$;

wherein $R^{13}$ is hydroxy, $C_1$–$C_4$alkoxy, fluoro, $C_1$–$C_6$alkyl, haloalkyl, haloalkoxy, —$NH_2$, —NH ($C_1$–$C_6$alkyl) or —N($C_1$–$C_6$alkyl)$_2$; or when both M and Q are $CR^4$, the $R^4$ groups are linked so that together with the interconnecting atoms, the $R^4$ groups form a fused 5- to 7-membered carbocyclic or heterocyclic ring which may be saturated, unsaturated or aromatic.

2. A compound according to claim 1 wherein L and U are —CH—.

3. A compound according to any preceding claim wherein W, Y and Z are each independently selected from hydrogen, methyl, ethyl, $CF_3$, $OCF_3$, $C_1$–$C_4$alkylthio, methoxy, ethoxy, chloro, fluoro and bromo.

4. A compound according to claim 3 wherein W and Z are hydrogen.

5. A compound according to any preceding claim wherein Y is methylthio.

6. A compound according to any preceding claim wherein M and Q are each independently s elected from —N— and —CH—.

7. A compound according to any preceding claim wherein $R^1$ and $R^2$ are each independently selected from hydrogen and $C_1$–$C_6$alkyl.

8. A compound according to claim 6 wherein $R^1$ is methyl and $R^2$ is hydrogen or methyl.

9. A compound according to claim 1 wherein the compound is selected from:

N-methyl-N-[(4-{[4-(methylsulfanyl)phenyl]sulfanyl}-3-pyridinyl)methyl]amine,

N,N-dimethyl-N-[(4-{[4-(methylsulfanyl)phenyl]sulfanyl}-3-pyridinyl)methyl]amine, N-methyl-N-[(3-{[4-(methylsulfanyl)phenyl]sulfanyl}-4-pyridinyl)methyl]amine, N,N-dimethyl-N-[(3-{[4-(methylsulfanyl)phenyl]sulfanyl}-4-pyridinyl)methyl]amine, N-methyl-N-[{3-[4-(methylsulfanyl)benzyl]-4-pyridinyl}methyl)amine, N,N-dimethyl-N-({3-4-(methylsulfanyl)benzyl]-4-pyridinyl}methyl)amine, N-methyl-N-({4-[4-(methylsulfanyl)benzyl]-3-pyridinyl}methyl)amine, and N,N-methyl-N-({4-[4-(methylsulfanyl)benzyl]-3-pyridinyl}methyl)amine, or pharmaceutically acceptable salts, solvates or polymorphs thereof.

10. A composition comprising a compound of formula (I) as claimed in any one of the preceeding claims, or pharmaceutically acceptable salts, solvates or polymorphs thereof, and a pharmaceutically acceptable diluent or carrier.

11. A compound of formula (I) as claimed in any one of the proceeding claims, or pharmaceutically acceptable salts, solvates or polymorphs thereof, for use as a medicament.

* * * * *